United States Patent
Abouraddy et al.

(10) Patent No.: US 9,488,775 B2
(45) Date of Patent: Nov. 8, 2016

(54) SYSTEMS AND METHODS FOR PRODUCING ROBUST CHALCOGENIDE OPTICAL FIBERS

(71) Applicant: University of Central Florida Research Foundation, Inc., Orlando, FL (US)

(72) Inventors: Ayman F. Abouraddy, Winter Park, FL (US); Guangming Tao, Orlando, FL (US); Soroush Shabahang, Orlando, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 23 days.

(21) Appl. No.: 14/398,548

(22) PCT Filed: May 3, 2013

(86) PCT No.: PCT/US2013/039489
§ 371 (c)(1),
(2) Date: Nov. 3, 2014

(87) PCT Pub. No.: WO2013/166401
PCT Pub. Date: Nov. 7, 2013

(65) Prior Publication Data
US 2015/0117828 A1    Apr. 30, 2015

Related U.S. Application Data (60) Provisional application No. 61/642,202, filed on May 3, 2012.

(51) Int. Cl.
*G02B 6/44* (2006.01)
*G02B 6/036* (2006.01)
*C03B 37/012* (2006.01)
*C03C 13/04* (2006.01)
*G02B 6/02* (2006.01)
(Continued)

(52) U.S. Cl.
CPC ......... *G02B 6/036* (2013.01); *C03B 37/01205* (2013.01); *C03B 37/01274* (2013.01); *C03B 37/026* (2013.01); *C03B 37/027* (2013.01); *C03C 13/043* (2013.01); *C03C 25/106* (2013.01); *C03C 25/18* (2013.01); *G02B 1/00* (2013.01); *G02B 1/105* (2013.01); *G02B 6/02395* (2013.01); *A61K 6/0273* (2013.01); *C03B 2201/86* (2013.01); *Y10T 428/239* (2015.01); *Y10T 428/24612* (2015.01); *Y10T 428/31533* (2015.04)

(58) Field of Classification Search
CPC .............. A61K 6/0273; A61K 6/0276; C03B 2201/86; C03B 2201/88; C03B 37/01274; C03B 2203/14; C03B 2203/16; C03B 2203/42; G02B 6/443; G02B 6/02395
See application file for complete search history.

(56) References Cited

U.S. PATENT DOCUMENTS

4,863,237 A  *  9/1989   France ................... 385/128
7,446,888 B2 * 11/2008   Stanke et al. ........... 356/625
(Continued)

*Primary Examiner* — Thomas A Hollweg
*Assistant Examiner* — Mary A El Shammaa
(74) *Attorney, Agent, or Firm* — William Greener; Bond, Schoeneck & King, PLLC (57) ABSTRACT

In one embodiment, a chalcogenide glass optical fiber is produced by forming a billet including a chalcogenide glass mass and a polymer mass in a stacked configuration, heating the billet to a temperature below the melting point of the chalcogenide glass, extruding the billet in the ambient environment to form a preform rod having a chalcogenide glass core and a polymer jacket, and drawing the preform rod.

9 Claims, 8 Drawing Sheets

(51) Int. Cl.
  *C03B 37/026* (2006.01)
  *C03B 37/027* (2006.01)
  *G02B 1/00* (2006.01)
  *G02B 1/10* (2015.01)
  *C03C 25/10* (2006.01)
  *C03C 25/18* (2006.01)
  *A61K 6/027* (2006.01)

(56) References Cited

U.S. PATENT DOCUMENTS

2006/0104582 A1* 5/2006 Frampton ........... B29C 47/0028
                                                            385/123
2009/0028488 A1* 1/2009 Monro et al. ................... 385/12
2009/0220785 A1* 9/2009 Monro et al. ................. 428/397

* cited by examiner

SYSTEMS AND METHODS FOR PRODUCING ROBUST CHALCOGENIDE OPTICAL FIBERS

CROSS-REFERENCE TO RELATED APPLICATION

This application is the 35 U.S.C. §371 national stage of, and claims priority to and the benefit of, PCT application PCT/US2013/039489, filed May 3, 2013, which claims priority to and the benefit of U.S. Provisional Application No. 61/642,202, filed on May 3, 2012, herein incorporated by reference in its entirety.

NOTICE OF GOVERNMENT-SPONSORED RESEARCH

This invention was made with Government support under contract/grant number ECCS-1002295, awarded by the National Science Foundation (NSF). The Government has certain rights in the invention.

BACKGROUND

There is currently great interest in optical fibers that can be used in mid-infrared (MIR) applications, such as the delivery of quantum cascade lasers. While silica optical fibers are commonplace and easy to obtain, such fibers have a limited window of wavelengths at which they are transparent and are highly absorbing of MIR light. Chalcogenide (ChG) glasses, on the other hand, are transparent across the entire infrared (IR) spectrum. While ChG can be used to produce optical fibers, ChG is extremely brittle and it is therefore difficult to produce robust ChG fibers.

Although silica fibers are made by drawing a preform in the ambient environment, ChG fibers cannot be produced in this manner because they are sensitive to the environment and oxidize easily. Instead, ChG fibers are typically produced by melting two ChG glasses (one for the core and one for the cladding) in a protected environment and drawing a fiber from a nozzle in a manner in which one glass surrounds the other. Once the fiber has been drawn, a thin polymer jacket can be applied. While this manufacturing method is feasible, it is difficult to maintain a uniform draw for long lengths (e.g., over 10 m) of the ChG glasses using the method because they are so soft during the draw process. In addition, it can be difficult to apply the polymer jacket because of the fragility of the ChG glass. Furthermore, because the polymer jacket is thin, the ChG optical fiber end product is quite fragile. Moreover, because of the conditions required to make the fiber, ChG optical fibers are extremely expensive.

From the above discussion, it can be appreciated that it would be desirable to have a way to produce robust ChG optical fibers with greater ease.

BRIEF DESCRIPTION OF THE DRAWINGS

The present disclosure may be better understood with reference to the following figures. Matching reference numerals designate corresponding parts throughout the figures, which are not necessarily drawn to scale.

DETAILED DESCRIPTION

As described above, it would be desirable to have a way to produce robust chalcogenide (ChG) optical fibers with greater ease. Disclosed herein are systems and methods for producing robust ChG optical fibers. In one embodiment, a billet is formed that comprises one or more ChG glass masses and a polymer mass that are arranged in a stacked configuration. In some embodiments, the ChG glass and polymer masses comprise independent cylindrical discs that are stacked in a predetermined order. The billet is heated to a temperature that enables viscous flow of the ChG glass but that does not melt the glass. Once the desired temperature is reached, the billet is extruded within the ambient environment to form an extruded rod that has a ChG core and a polymer jacket that protects the ChG from the environment and enables further processing. The rod can then be drawn to obtain an optical fiber having a desired diameter. Optionally, further polymer material can be applied to the rod or the fiber to form a relatively thick jacket that provides greater mechanical protection to the ChG glass.

In the following disclosure, various specific embodiments are described. It is to be understood that those embodiments are example implementations of the disclosed inventions and that alternative embodiments are possible. All such embodiments are intended to fall within the scope of this disclosure.

A one-step, multi-material extrusion fabrication approach for the production of ChG optical fibers is described below. With this approach, composite ChG/polymer preforms are produced that can be drawn into robust fibers. A billet comprising a polymer and ChG is extruded into a preform having a built-in polymer jacket. The polymer does not participate in the optical functionality of the fiber, which is dictated by the ChG alone. The resulting optical fibers can also be used to form robust, high-index-contrast, submicron-core-diameter tapers suitable for nonlinear optical applications without removing the polymer.

Figure 1:
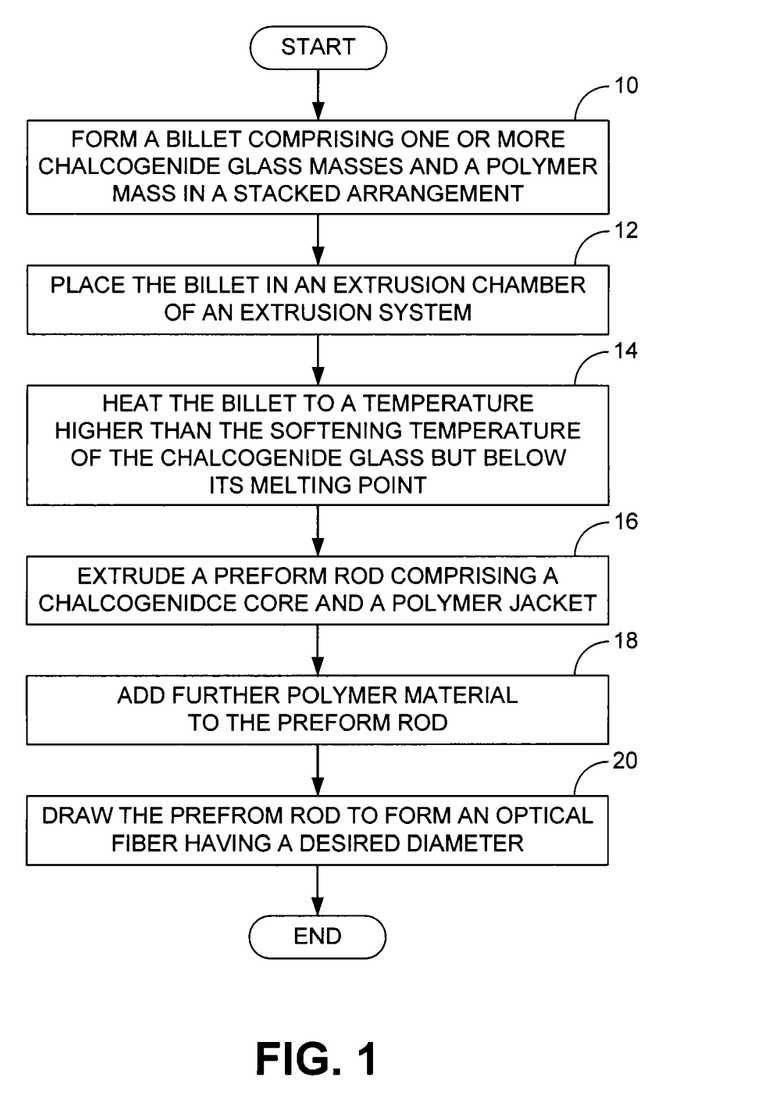
FIG. 1 is a flow diagram of an embodiment of a method for producing robust chalcogenide optical fibers.
Figure 2:
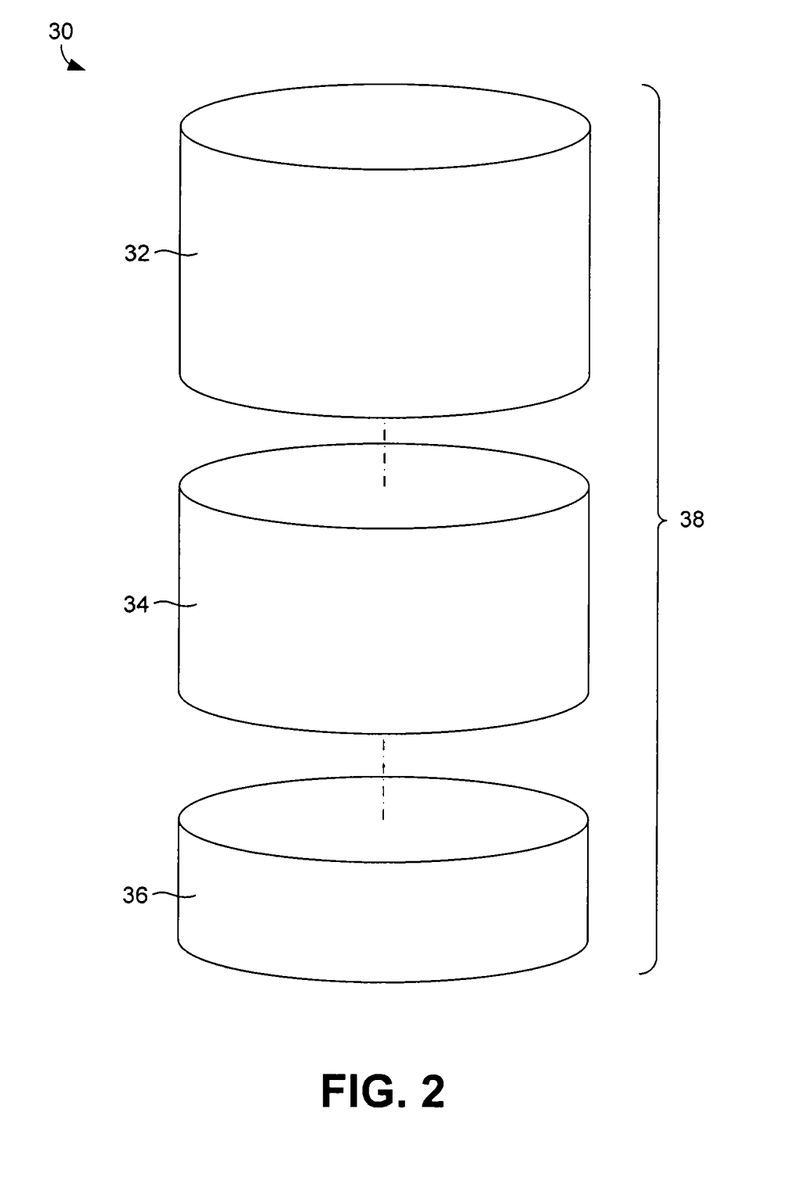
FIG. 2 is an exploded perspective view of a first embodiment of a billet that can be used to produce robust chalcogenide optical fibers.

FIG. 1 is a flow diagram that describes an embodiment of a method for producing a robust ChG optical fiber. Beginning with block 10 of the figure, a billet is formed that comprises one or more ChG glass masses and a polymer mass in a stacked arrangement. FIG. 2 illustrates an example billet 30 in an exploded view. In the example of FIG. 2, the billet 30 includes a first ChG glass mass 32, a second ChG glass mass 34, and a polymer mass 36 that together form a stack 38 of masses. The first ChG glass mass 32 is at the top of the stack 38, the second ChG glass mass 32 is in the middle of the stack, and the polymer mass 36 is positioned at the bottom of the stack. The order of the masses dictates the positions that the materials of the billet 30 will occupy in the optical fiber. Specifically, the top mass will form a core of the fiber, the middle mass will form an intermediate layer (cladding) of the fiber, and the bottom mass will form an outer layer (jacket) of the fiber.

In some embodiments, the first ChG glass mass 32 can comprise $As_2Se_3$ or $As_2Se_{1.5}S_{1.5}$ and the second ChG glass mass 34 can comprise $As_2S_3$. In some embodiments, the polymer comprises a thermally compatible thermoplastic polymer such as polyethersulfone (PES), polyetherimide (PEI), polysulfone, polycarbonate, or cyclo-olefin polymer or copolymer.

In the example of FIG. 2, each mass is formed as a cylindrical mass having a circular cross-section. In some embodiments, the diameter of the masses is approximately 25 to 50 mm. The relative heights of the masses dictate the nature of the optical fiber that will be formed. Specifically, the ratios between the heights of the masses will dictate the ratios of the materials across the cross-section of the fiber. Accordingly, the heights of the masses can be varied to vary the cross-sectional ratios of the fiber materials. In some embodiments, the first ChG glass mass 32 is approximately 5 to 30 mm tall, the second ChG glass mass 34 is approximately 5 to 30 mm tall, and the polymer mass 36 is approximately 5 to 30 mm tall.

Figure 3:
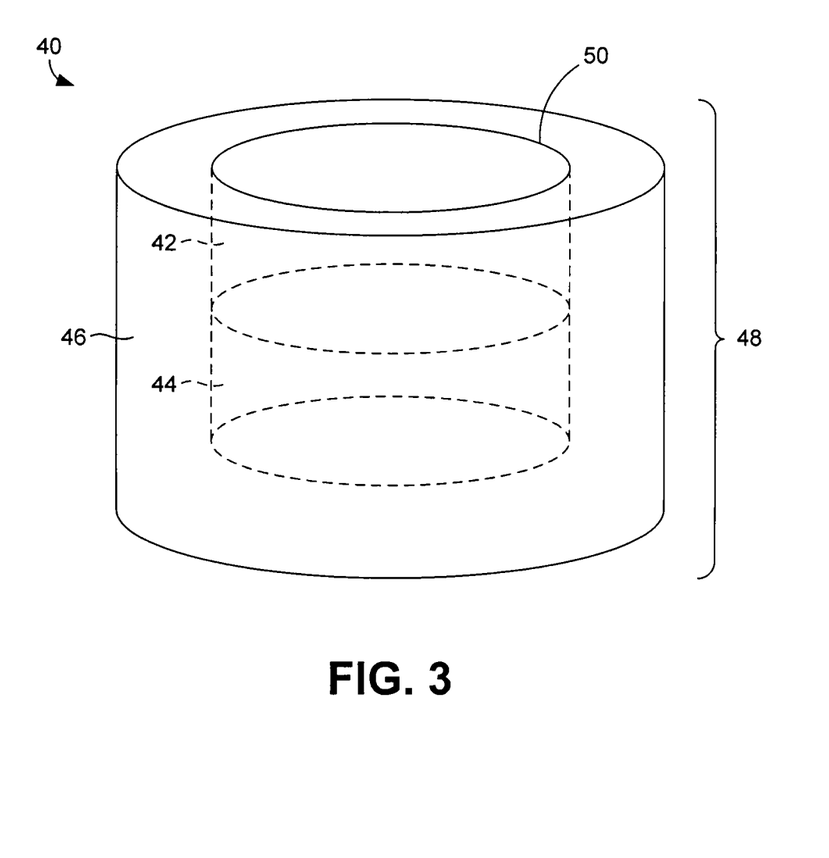
FIG. 3 is a perspective view of a second embodiment of a billet that can be used to produce robust chalcogenide optical fibers.

FIG. 3 illustrates an alternative billet 40. The billet 40 also includes a first ChG glass mass 42, a second ChG glass mass 44, and a polymer mass 46 that together form a stack 48 of masses. The masses can be made of the same materials described above in relation to FIG. 2. In the embodiment of FIG. 3, however, the polymer mass 46 includes a void 50 in which the ChG masses 42, 44 are disposed in a stacked configuration in which the ChG glasses are surrounded on all sides by polymer and therefore will not come into contact with the walls of an extruder. With this configuration, the first ChG glass mass 42 (top mass) will form the core of the fiber, the second ChG mass 44 (middle mass) will form the intermediate layer (cladding) of the fiber, and the polymer mass 46 (bottom mass) will form the outer layer (jacket) of the fiber.

As in the embodiment of FIG. 2, each mass in the billet 40 is formed as a cylindrical mass having a circular cross-section. In some embodiments, the outer diameter of the polymer masses is approximately 25 to 50 mm and the diameter of the ChG glass masses 42, 44 is approximately 10 to 25 mm. In some embodiments, the first ChG glass mass 42 is approximately 5 to 15 mm tall, the second ChG glass mass 44 is approximately 5 to 15 mm tall, and the polymer mass 46 is approximately 25 to 60 mm tall.

Figure 4:
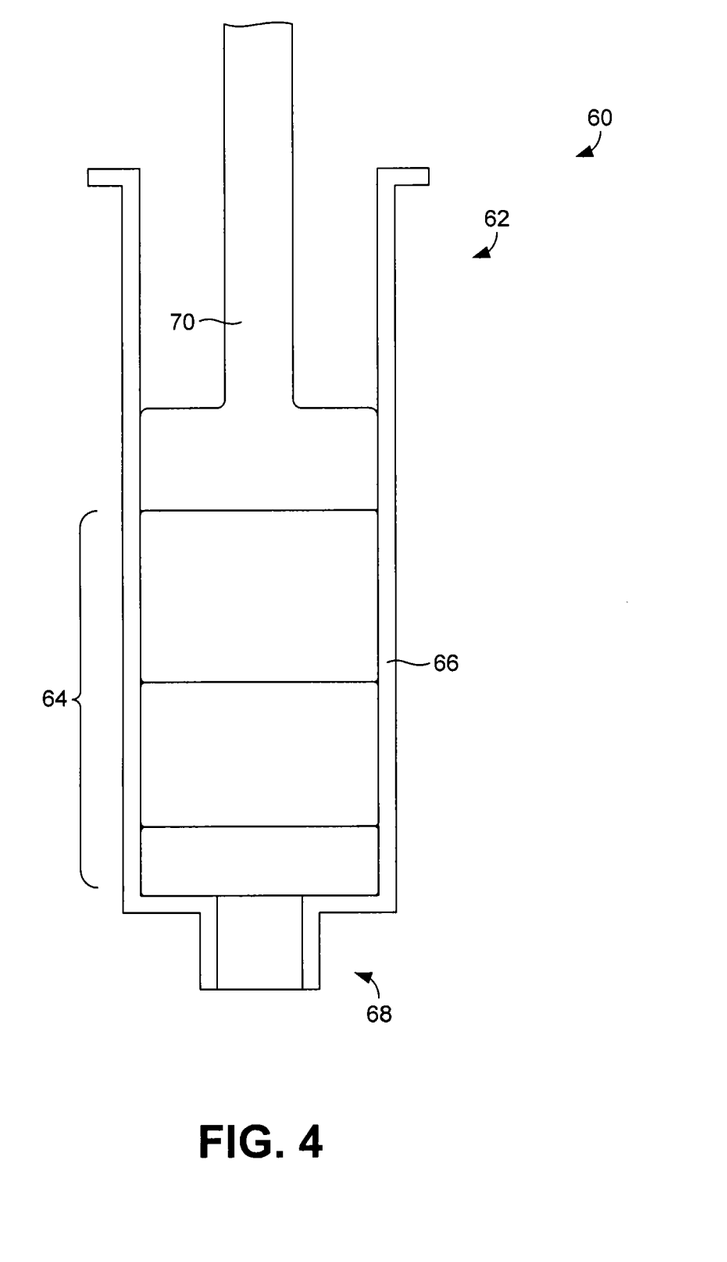
FIG. 4 is a schematic view of an extrusion system that can be used to produce robust chalcogenide optical fibers.

With reference back to FIG. 1, the billet, irrespective of its particular form, can be placed within an extrusion chamber of an extrusion system, as indicated in block 12. FIG. 4 illustrates an example of an extrusion system 60, which can be positioned within a furnace (not shown). The system 60 includes an extrusion chamber 62 in which an example billet 64 has been placed. In embodiments in which the billet 64 is cylindrical, the extrusion chamber 62 can be formed by a cylindrical sleeve 66 that has an inner diameter of approximately 30 to 46 mm. The sleeve 66 includes a circular die 68 through which the billet 64 is extruded. In some embodiments, the die 68 has an inner diameter of approximately 6 to 20 mm. The extrusion system 60 further includes a piston 70 that is used to drive the billet material through the die.

With reference to block 14 of FIG. 1, the billet is next heated to a temperature that is higher than the softening temperature of the ChG glass but lower than the melting point of the glass. In some embodiments, the billet is heated to a temperature of approximately 180 to 330° C. Once the billet is heated to that temperature, viscous flow is possible. Therefore, as indicated in block 16, the billet can be extruded to form a preform rod that comprises a ChG core and a polymer jacket. In embodiments in which the billet comprises two masses of ChG glass, the rod will further comprise a ChG glass cladding positioned between the core and the jacket. In some embodiments, the extrusion can be performed using approximately 90 to 1000 pounds of force to extrude the billet at a rate of approximately 0.3 to 0.7 mm/minute. Such extrusion under pressure enables the use of lower temperatures and higher viscosities as compared to fiber drawing, thereby reducing glass crystallization. The outer diameter of the rod and the diameter of the core will depend upon the inner diameter of the die of the extrusion system. In some embodiments, the preform rod has an outer diameter of approximately 2 to 20 mm and a core diameter of approximately 500 to 6000 μm.

At this point, further polymer material can be added to the preform, if desired, as indicated in block 18. Such additional material provides further mechanical stability to the preform that enables processing of the rod into an optical fiber. In some embodiments, a thin film of polymer can be rolled onto the rod or the rod can be inserted into a polymer tube.

Next, with reference to block 20, the preform rod can be drawn to form an optical fiber having the desired diameter. In some embodiments, the rod can be drawn to form an optical fiber having an outer diameter of approximately 0.5 to 2 mm, a core diameter of approximately 2 to 500 μm, a cladding having a thickness of approximately 1 to 500 μm, and a jacket having a thickness of approximately 200 to 1000 μm. The jacket can be called a "built-in" jacket because the jacket material was added to the fiber (or to the rod) prior to the final drawing.

Figure 5:
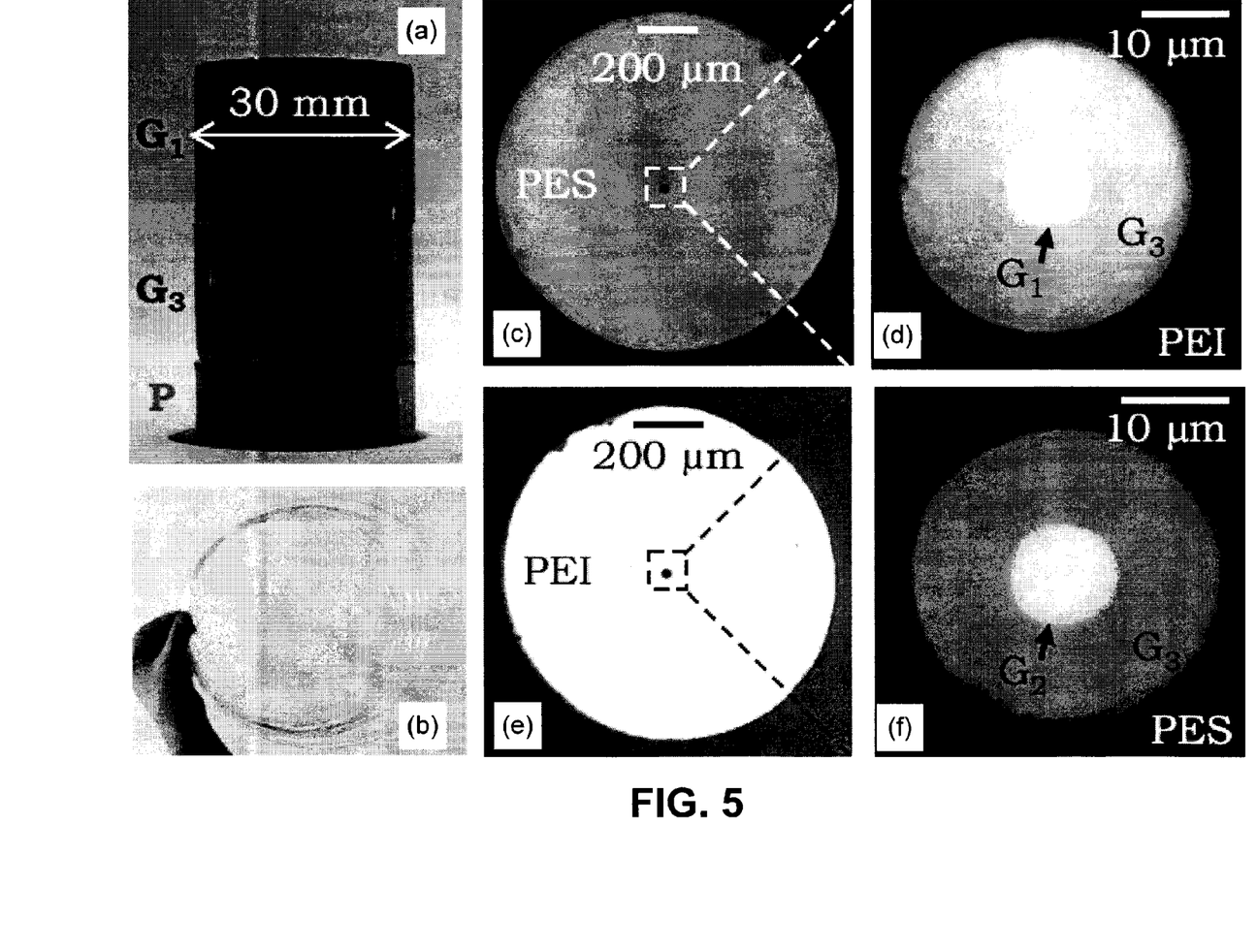
FIG. 5 includes images of (a) a vertically-stacked billet, (b) a drawn GGP fiber, (c) and (e) transmission optical micrographs of the fiber cross sections, and (d) and (f) reflection micrographs of the core.

ChG optical fibers were fabricated using the methodologies described above. A preform was made with a first ChG glass for the core and a second ChG glass for the cladding. A vertically-stacked billet was formed comprising polished discs placed atop each other as shown in FIG. 5(a). The top disc comprised one of $As_2Se_3$ (G1) and $As_2Se_{1.5}S_{1.5}$ (G2), the middle disc comprised $As_2S_3$ (G3), and the bottom disc comprised PES or PEI(P). The three glasses had measured indices of 2.904, 2.743, and 2.472 at 1.55 μm, respectively. The large index-contrast between the ChG glasses was chosen in order to test the limits of the extrusion process and to produce high-index-contrast nano-tapers described below.

The billet was heated and extruded to form an extruded preform that comprised nested shells with a ChG core, a ChG cladding, and a polymer jacket. This structure is referred to hereafter as GGP. The polymer protected the ChG from coming in contact with the die during extrusion or subsequently with the ambient environment. No separation between the layers in the preforms or in the subsequently drawn fibers was observed. The relatively large thermal expansion coefficient of the polymer eliminated small gaps from the preform that inevitably exist at interfaces in the billet.

Each preform was then drawn into a cane and a 10-cm long section of the cane was inserted into a polymer tube, which in turn was drawn into approximately 100 m of continuous, robust, 1-mm outer diameter, 10-μm core diameter fiber shown in FIG. 5(b). Cross-sections of the two GGP fibers, G1-G3-PEI and G2-G3-PES, are shown in FIGS. 5(c) and (d) and FIGS. 5(e) and (f), respectively. The ChG in the latter two figures represents less than 0.1% of the fiber volume: 10 km of this fiber contains approximately 30 g of glass. The core-to-cladding diameter ratio was approximately 1:3. This ratio can be controlled by changing the thicknesses of the discs in the billet and the pressure applied during extrusion. Reducing this ratio, however, reduces the yield of the useful preform length. The built-in polymer jacket facilitated the fiber drawing compared to bare-glass-fiber drawing and helped avoid oxidization of the ChG. The fiber transmission losses (for a GGP fiber with $As_2Se_3$ core) evaluated by cutback measurements were approximately 10.9 dB/m at 1.55 μm (using a laser diode) and approximately 7.8 dB/mat at 2 μm (using a Tm-doped fiber laser). The loss at the moment was limited by the purity of the glass.

Figure 6:
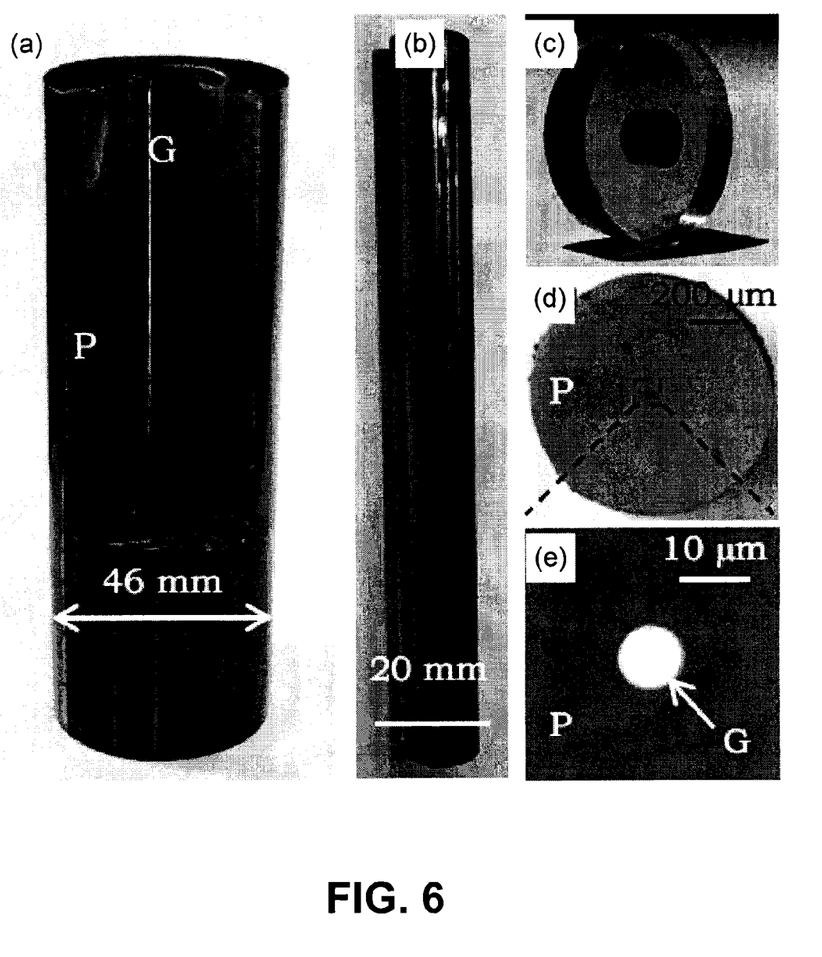
FIG. 6 includes images of (a) a hybrid polymer and ChG billet, (b) a section of an extruded preform, (c) a disc cut from the extruded preform, and (d) and (e) reflection optical micrographs of the fiber cross-section and core, respectively.

Fibers comprising a ChG core and a polymer jacket without an intermediate cladding were also formed using an extrusion process. ChG rods were prepared from commercial glass (AMI, Inc.) by melt-quenching, and polymer rods were prepared by thin-film processing. A ChG-core (G1), polymer-jacket (PES) preform was formed (FIGS. 6(b) and (c)) using a nested billet (FIG. 6(a)) that comprised a ChG rod (11-mm diameter, 60-mm length) provided within a polymer tube (46-mm outer diameter, 140-mm length). This structure is referred to as GP. The drawn fiber is illustrated in FIGS. 6(d) and 6(e). In particular, a reflection optical micrograph of the fiber cross-section is shown in FIG. 6(d) and the core is shown in the detail view of FIG. 6(e).

Figure 7:
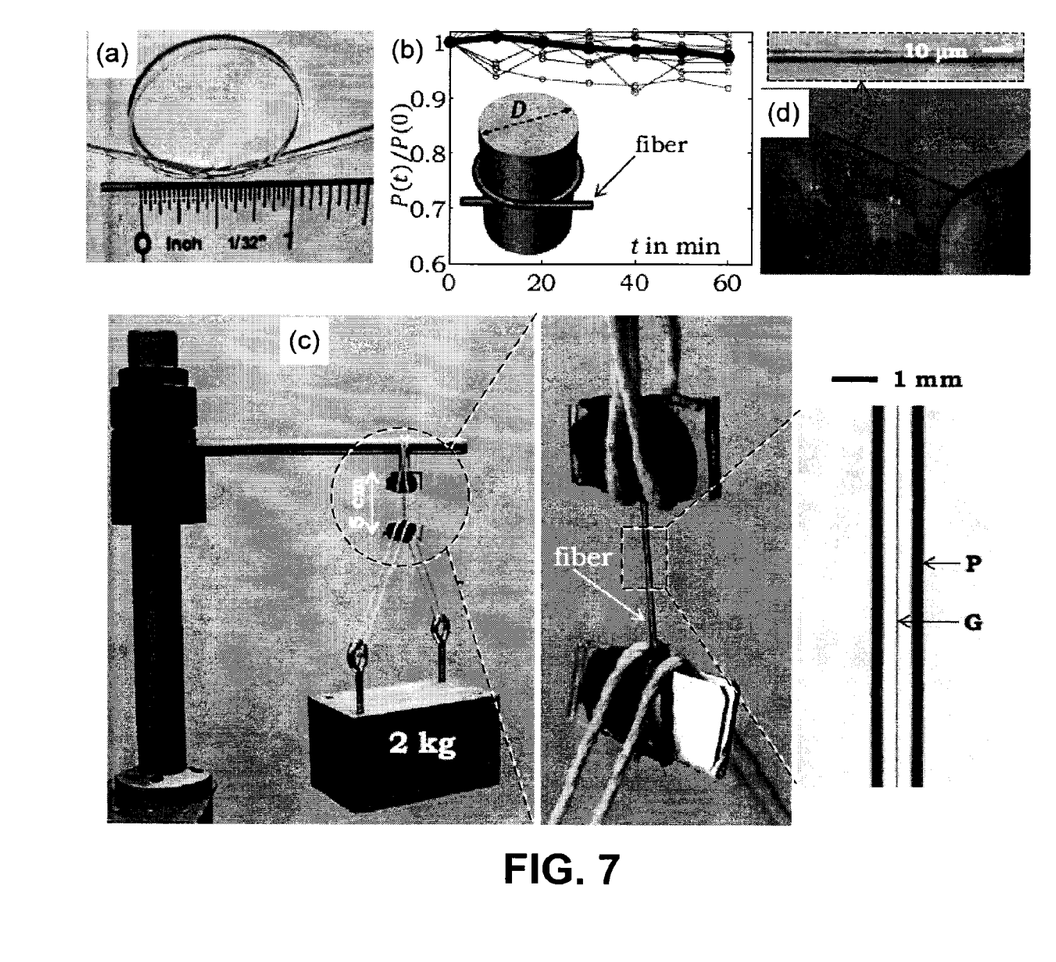
FIG. 7 includes images of (a) a 1-mm-diameter fiber tied in a 1-inch diameter knot, (b) a plot of transmission versus time for 10 fibers after bending the fiber with D=0.5 inch bend diameter (the thick curve is the average of all the measurements), (c) a 2-kg weight hanging from a 5-cm-long fiber (insets to the right show the hanging mechanism), and (d) a robust multi-material taper (inset above is a micrograph of the taper center).

The robustness of the above-described ChG fibers is illustrated in FIG. 7. The transmission at 1.55 μm over time was measured after bending a GP fiber for 10-minute intervals. There was no change for 1-inch bend diameters and larger, and no plastic memory was observed in knots with diameters larger than 1 inch (FIG. 7(a)). Results for a 0.5-inch bend diameter are plotted in FIG. 7(b). The transmission did not decrease after an hour by more than 10% (5% on average). The effect of axial stress on optical transmission was also investigated. A 2-kg weight was hung from multiple 5-cm-long GP fiber sections (FIG. 7(c)) for 18 hours each and the transmission at 1.55 μm was measured. The transmission was unaffected in this experiment. The fiber thus withstood 14.6 Kpsi (~25.5 MPa) with no change in its performance over this extended period of time. This sets a lower limit on the fiber strength. Although the ChG diameter was only 10 μm, the polymer jacket nevertheless enabled convenient handling and reduced ageing of the fibers. Therefore, the optical properties of the fiber are determined by the ChG, while the mechanical properties are determined by the polymer. Separating the functionalities in this manner enables them to be independently optimized.

A unique advantage of the thermally-compatible built-in polymer jacket is that it provides a mechanical scaffold for producing robust tapers without first removing the polymer. ChG nano-tapers combine high optical nonlinearities with dispersion control but are hampered by their extreme fragility. The robustness of multi-material tapers is highlighted in FIG. 7(d), which shows a taper with a core diameter of 25 nm and an outer diameter of 3 μm.

Figure 8:
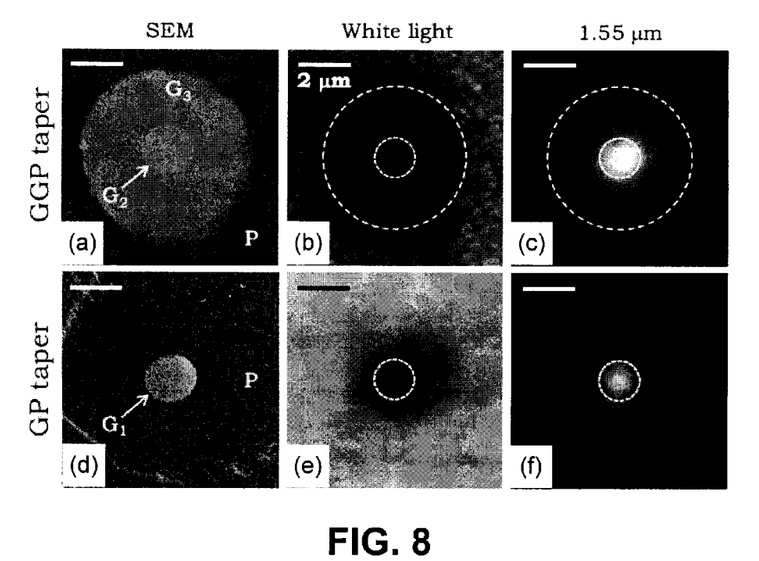
FIG. 8 includes images of characterization of GGP tapers ((a)-(c)) and GP tapers ((d)-(f)). FIGS. (a) and (d) are SEM micrographs of the cross sections, FIGS. (b) and (e) are white-light images, and FIGS. (c) and (f) are 1.55-μm laser light near-field intensity images.

The GP and GGP tapers were characterized in three ways after cutting the taper at its center where the diameter is smallest ($d_{min}$=1.4 μm for the core in both tapers). First, the structure was determined using SEM imaging, confirming that size reduction occurred at the same rate throughout the cross-section during tapering (FIGS. 8(a) and (d)). Second, the ChG-polymer interface was determined by transmitting white light (coupled from the untapered end, $d_o$=10 μm) because the polymer is transparent in the visible and the ChG is not (FIGS. 4(b) and (e)). Third, the modal structure was determined by transmitting 1.55-μm CW light (from a laser diode) through the core (FIGS. 4(c) and (f)). The mode was confined to the glass in the GGP taper due to the high core-cladding index contrast and extended into the polymer in the GP taper. The mechanical strength of the polymer jacket is thus harnessed without compromising the optical functionality of the taper.

Figure 9:
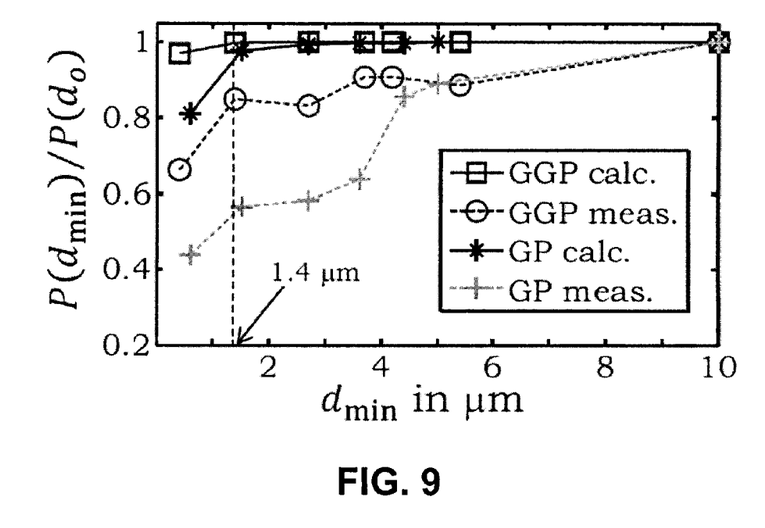
FIG. 9 is a plot of the measured and calculated optical transmission at 1.55 μm for GGP and GP tapers with different $d_{min}$ normalized with respect to the untapered fiber with $d_o$=10 μm. The dashed vertical line corresponds to $d_{min}$=1.4 μm used in FIGS. 8(a)-(f).

The transmission in tapers of the same length (2.1 cm) with $d_{min}$ from 10 μm down to 400 nm for GGP and GP tapers was measured and the results were compared in FIG. 9 to calculations performed using the scalar beam propagation method in OptiBPM 10.0 (Optiwave). The transverse simulation window was 50×50 μm$^2$ and the step size was 0.1 μm in all three dimensions with perfectly matched layer boundary condition on all sides. The measured taper profile and realistic material losses were used. The higher loss in the GP taper was due to absorption of the evanescent tail in the polymer, while in the GGP taper the light remained confined to the ChG. The measured losses were higher than predicted but this was attributed to scatterers in the glass whose impact increases at smaller diameters, deformations in the cross-section during tapering, and surface roughness at the interfaces (particularly for the GP taper).

In conclusion, a novel one-step multi-material preform extrusion process has been developed that produces hybrid ChG/polymer preforms that are drawn into robust infrared fibers and tapers. The process helps obviate the mechanical limitations of ChG fibers and enables optimizing the optical properties for nonlinear applications.

We claim:

1. A method for producing a chalcogenide glass optical fiber, the method comprising:
    forming a billet including at least two chalcogenide glass masses and a polymer mass in a stacked configuration, wherein one of the chalcogenide glass masses is a fiber core material and at least one other of the chalcogenide glass masses is a fiber cladding material, further wherein each of the at least two chalcogenide glass masses is characterized by a known softening temperature;
    heating the billet to a temperature to above the highest one of the known softening temperatures of the chalcogenide glass masses;
    extruding the billet to form a preform rod having a chalcogenide glass core, at least one chalcogenide glass cladding surrounding the core, and a polymer jacket surrounding the at least one chalcogenide glass cladding; and
    drawing, in a single operational step, an optical fiber from the preform rod having a single chalcogenide glass core, at least one chalcogenide glass cladding surrounding the single core, and a polymer jacket surrounding an outermost one of the at least one chalcogenide glass cladding.

2. The method of claim 1, wherein the at least two chalcogenide glass masses are stacked on top of the polymer mass in the billet.

3. The method of claim 2, wherein the at least two chalcogenide glass masses are completely encircled by the polymer mass in the billet.

4. The method of claim 3, wherein the at least two chalcogenide glass masses are disposed within a void of the polymer mass.

5. The method of claim 1, comprising heating the billet to a temperature of between 180 to 330° C.

6. The method of claim 1, comprising extruding the billet with a force between 90 to 1000 pounds.

7. The method of claim 1, further comprising adding additional polymer material to the preform rod prior to drawing.

8. The method of claim 1, comprising extruding the billet in an ambient environment.

9. The method of claim 1, comprising drawing, in a single operational step, the optical fiber characterized by a tensile stress yield greater than 10 Mpa.

\* \* \* \* \*